US011344260B2

(12) United States Patent
Egea Guerrero et al.

(10) Patent No.: US 11,344,260 B2
(45) Date of Patent: May 31, 2022

(54) PREDICTING THE RISK OF DEATH OR VASOSPASM IN A PATIENT WITH A SUBARACHNOID HEMORRHAGE

(71) Applicants: SERVICIO ANDALUZ DE SALUD, Seville (ES); UNIVERSIDAD DE SEVILLA, Seville (ES)

(72) Inventors: Juan José Egea Guerrero, Seville (ES); Marcin Wojciech Balcerzyk, Seville (ES)

(73) Assignees: SERVICIO ANDALUZ DE SALUD, Seville (ES); UNIVERSIDAD DE SEVILLA, Seville (ES)

( * ) Notice: Subject to any disclaimer, the term of this patent is extended or adjusted under 35 U.S.C. 154(b) by 166 days.

(21) Appl. No.: 16/640,303

(22) PCT Filed: Jul. 30, 2018

(86) PCT No.: PCT/ES2018/070539
§ 371 (c)(1),
(2) Date: Jul. 30, 2020

(87) PCT Pub. No.: WO2019/025656
PCT Pub. Date: Feb. 7, 2019

(65) Prior Publication Data
US 2020/0352523 A1 Nov. 12, 2020

(30) Foreign Application Priority Data

Jul. 31, 2017 (ES) .............................. ES201730998

(51) Int. Cl.
*G06K 9/00* (2022.01)
*A61B 5/00* (2006.01)
(Continued)

(52) U.S. Cl.
CPC .......... *A61B 5/7275* (2013.01); *A61B 5/0042* (2013.01); *G06T 3/60* (2013.01);
(Continued)

(58) Field of Classification Search
CPC ................................................... A61B 5/7275
See application file for complete search history.

(56) References Cited

U.S. PATENT DOCUMENTS 10,960,011 B2    3/2021   Wittel et al.
2014/0316758 A1* 10/2014  Yagi ....................... A61B 5/026
                                                                  703/9
(Continued)

FOREIGN PATENT DOCUMENTS

CN       101238987 A     8/2008
CN       101916443 B     10/2012

OTHER PUBLICATIONS

Weir et al. (NPL: "Aneurysmal Subarachnoid Hemorrhage in Patients with Hunt and Hess Grade 4 or 5: Treatment Using the Guglielmi Detachable Coil System" AJNR Am J Neuroradiol 24:585-590, Apr. 2003). (Year: 2003).*
(Continued)

*Primary Examiner* — Oneal R Mistry
(74) *Attorney, Agent, or Firm* — Seed IP Law Group LLP

(57) ABSTRACT

The invention describes a method for predicting or prognosticating the risk of death or vasospasm in a patient with a subarachnoid hemorrhage, which comprises the following steps: performing a clinical assessment of the patient according to the Hunt and Hess scale and the World Federation of Neurosurgeons (WFNS) scale; obtaining a computerised axial tomography image of the patient's skull; normalising the image obtained according to a standard skull template; obtaining a region corresponding to intracranial blood by segmenting the normalised image; calculating at least the (Continued)

following parameters of the region of cranial blood obtained: total volume, fractal dimension and surface-volume ratio; and determining the probability of death or vasospasm in the patient according to at least the parameters calculated.

7 Claims, 6 Drawing Sheets

(51) Int. Cl.
　　　*G06T 7/136*　　　(2017.01)
　　　*G06T 7/11*　　　(2017.01)
　　　*G06T 3/60*　　　(2006.01)
　　　*G06T 7/00*　　　(2017.01)

(52) U.S. Cl.
　　　CPC .............. *G06T 7/0014* (2013.01); *G06T 7/11* (2017.01); *G06T 7/136* (2017.01); *G06T 2207/10081* (2013.01); *G06T 2207/30016* (2013.01); *G06T 2207/30101* (2013.01)

(56) References Cited

U.S. PATENT DOCUMENTS

| | | | |
|---|---|---|---|
| 2015/0302139 A1* | 10/2015 | Sankaran | A61B 5/026 703/20 |
| 2018/0310854 A1* | 11/2018 | Geva | A61B 5/7242 |
| 2018/0366225 A1* | 12/2018 | Mansi | H04L 67/12 |
| 2019/0331684 A1 | 10/2019 | Luque Huertas et al. | |
| 2019/0358467 A1 | 11/2019 | Velázquez Miranda et al. | |
| 2019/0365675 A1 | 12/2019 | Orío Ortiz et al. | |
| 2020/0158732 A1 | 5/2020 | Castaño Fuentes et al. | |
| 2020/0215227 A1 | 7/2020 | Carriel Araya et al. | |
| 2020/0281897 A1 | 9/2020 | Pérez Simón et al. | |
| 2021/0154352 A1 | 5/2021 | Campos Cuerva et al. | |
| 2021/0207089 A1 | 7/2021 | Fernández Muñoz et al. | |

OTHER PUBLICATIONS

"Anmeurysmal Subarachnoid Hemorrhage in Patients with Hunt and Hess Grade 4 or 5: Preatment Using the Guglielmi Detachable Coil System" AJNR Am J Neuroradiol 24:585-590, Apr. 2003) (Year: 2003).*

Boers et al., "Automatic Quantification of Subarachnoid Hemorrhage on Noncontrast CT," *AJNR Am. J. Neuroradiol* 35:2219-2286, Dec. 2014.

Broderick et al., "Volume of Intracerebral Hemorrhage. A Powerful and Easy-to-Use Predictor of 30-Day Mortality," *Stroke* 24(7):987-993, Jul. 1993.

Charpentier et al., "Multivariate Analysis of Predictors of Cerebral Vasospasm Occurrence After Aneurysmal Subarachnoid Hemorrhage," *Stroke*:1402-1408, Jul. 1999.

Chen et al., "Segmentation of the thrombus of giant intracranial aneurysms from CT angiography scans with lattice Boltzmann method," *Medical Image Analysis* 18:1-8, Sep. 4, 2013 (2014).

Li et al., "Automatic Detection of the Existence of Subarachnoid Hemorrhage from Clinical CT Images," *J. Med. Syst.* 36:1259-1270, Sep. 9, 2010 (2012).

Munakomi et al., "Role of computed tomography scores and findings to predict early death in patients with traumatic brain injury: A reappraisal in a major tertiary care hospital in Nepal," *Surgical Neurology International* 7(23):Feb. 19, 2016 (6 pages).

Prakash et al., "Segmentation and quantification of intra-ventricular/cerebral hemorrhage in CT scans by modified distance regularized level set evolution technique," *Int. J. Comput. Assist. Radiol. Surg.* 7(5):785-798, Sep. 2012, Author manuscript; available in PMC Sep. 1, 2013 (24 pages).

Rorden et al., "Age-specific CT and MRI templates for spatial normalization," *Neuroimage* 61(4):957-965, Jul. 16, 2012, Author manuscript; available in PMC Jul. 16, 2013 (20 pages).

Shahangian et al., "Automatic brain hemorrhage segmentation and classification algorithm based on weighted grayscale histogram feature in a hierarchical classification structure," *Biocybernetics and Biomedical Engineering* 36:217-232, Dec. 17, 2015 (2016).

U.S. Appl. No. 17/267,418.
U.S. Appl. No. 17/281,520, filed Mar. 30, 2021.
U.S. Appl. No. 17/599,463, filed Sep. 28, 2021.
U.S. Appl. No. 17/611,460.

* cited by examiner

PREDICTING THE RISK OF DEATH OR VASOSPASM IN A PATIENT WITH A SUBARACHNOID HEMORRHAGE

OBJECT OF THE INVENTION

The present invention is generally comprised in the field of medicine, and more particularly in the field of emergency medical care for patients with a subarachnoid hemorrhage.

The object of the present invention is a new method which allows predicting the probability of death or vasospasm in patients afflicted with a subarachnoid hemorrhage.

BACKGROUND OF THE INVENTION

Subarachnoid hemorrhage (SAH) consists of bleeding into the space existing between the structures of the meninges surrounding the brain. This phenomenon commonly occurs after the spontaneous rupture of an aneurysmal cerebral artery. Its incidence is estimated to be between 4-28/100,000 people and is the most common cause of sudden death due to stroke. Despite having make important scientific efforts aimed at improving the outcomes of patients suffering an SAH, the rate of fatal outcomes are still high. In summary, it is a serious pathology with an approximate mortality of 20 to 40% of patients admitted to a hospital, and more than 8 to 15% mortality in the first few minutes or hours in the pre-hospitalization stage.

The most common signs and symptoms usually appear in a sudden manner in an individual who generally did not present any previous neurological disturbances. Headache, which is the most common symptom, is described as being of sudden onset, intense, and unusual. It may also be referred to as neck pain and light sensitivity. It commonly presents with nausea and vomiting. However, it is not always characteristic, given that it may have any location, may be localized or general, may be mild and spontaneously resolve, or may be alleviated with non-narcotic analgesics.

Currently, the diagnosis of subarachnoid hemorrhage is based on a compatible clinical picture plus the presence of blood in the subarachnoid space. The presence of blood in the subarachnoid space is detected by performing a cranial computerized axial tomography scan (CAT) scan. Precision in the identification of SAH is highly dependent on the quality of the computerized tomography scan and on the skill of the medical professional who interprets it. It is easy for inexperienced doctors to not see subtle abnormalities.

Multiple studies have determined that the prognosis of a patient with an SAH is directly related to the patient's neurological condition upon admission, which is stratified according to the Hunt and Hess scale (Table 1) and the World Federation of Neurosurgeons scale (WFNS) (Table 2), and to the magnitude of initial bleeding, which is stratified according to the Modified Fisher scale (Table 3).

TABLE 1

Hunt and Hess Scale

| | |
|---|---|
| Grade I | Asymptomatic, mild headache, or slight nuchal rigidity |
| Grade II | Moderate to severe headache, nuchal rigidity, cranial nerve palsy. |
| Grade III | Sluggishness, confusion, mild focal neurologic deficit. |
| Grade IV | Stupor, moderate to severe hemiparesis, early decerebrate rigidity or neurovegetative disturbances |
| Grade V | Coma, decerebrate rigidity |

TABLE 2

World Federation of Neurosurgeons Scale (WFNS)

| | | |
|---|---|---|
| Grade I | Glasgow 15/15 | Focal deficit absent. |
| Grade II | Glasgow 13-14/15 | Focal deficit absent. |
| Grade III | Glasgow 13-14/15 | Focal deficit present. |
| Grade IV | Glasgow 7-12/15 | Focal deficit present or absent. |
| Grade V | Glasgow 3-6/15 | Focal deficit present or absent. |

TABLE 3

Modified Fisher scale

| | Subarachnoid Hemorrhage | Intraventricular Hemorrhage |
|---|---|---|
| Grade 0 | Absent | Absent |
| Grade 1 | Thin | Absent |
| Grade 2 | Thin or Absent | Present |
| Grade 3 | Thick | Absent |
| Grade 4 | Thick | Present |

Nevertheless, the high morbidity and mortality of SAH is largely due to complications occurring after the initial bleeding. Namely, vasospasm cerebral, which usually presents after the day of bleeding (after the fourth day of progression), is one of the most feared and most difficult to foresee developmental complications and is responsible for the neurologic impairment of the patient and even death in 15-20% of patients.

Up until now, the detection of the onset of vasospasm cerebral has been performed by continuous clinical examination of the patient, sonographic recordings of cerebral arteries, or even by cerebral angiography. Unfortunately, the vasospasm do not always present in an evident manner in the patient and their late detection triggers sever sequelae in patients, as the effects of the lack of blood to an already injured brain after an SAH cannot be reversed.

With said drawbacks in mind, finding new tools which offer useful and accurate information would be extremely useful in being able to estimate the risk that each patient has of suffering of these complications or even dying. Having objective data which allows stratifying patients according to their level of severity would allow preventing the occurrence of disabling sequelae and to safeguard the life of the patients. Moreover, it would allow proportionally improving the efficiency of hospital resources both from the perspective of the location of the patient (ICU, Stroke Unit or hospitalization floor), or even providing effective early treatment of the complications of vasospasms after the SAH.

DESCRIPTION OF THE INVENTION

The method of the present invention solves the aforementioned by obtaining a set of objective parameters from computerized tomography (CAT) scan image of the patient's skull, and based on said parameters it is possible to predict the probability of death of the patient or of said patient suffering a vasospasm. This method can be carried out in a completely or partially automated manner by processing means, thereby reducing errors due to a lack of attention or lack of skill of the medical professional.

The method of the present invention fundamentally comprises the following steps:

1) Performing a clinical assessment of the patient according to the Hunt and Hess scale and the WFNS scale, and determining their sex and age.

2) Obtaining a computerized axial tomography (CAT) scan image of the patient's skull.
3) Normalizing the image of the patient's skull according to a standard skull template.
4) Obtaining a region corresponding to intracranial blood by segmenting the normalized image of the patient's skull.
5) Calculating at least the following parameters of the region of intracranial blood obtained: total volume, fractal dimension, and surface-volume ratio.
6) Determining the probability of death or vasospasm in the patient according to at least the parameters calculated.

Each of the steps of the method is described below in greater detail.

1. Clinical Assessment with the Hunt and Hess Scale and WFNS Scale.

The doctor on duty assesses the patient according to the Hunt and Hess scale and the WFNS scale. This step is usually performed when the patient comes to the hospital, usually the emergency room. The sex and age of the patient can also be determined at this time.

2. Obtaining a Computerized Axial Tomography (CAT) Scan Image

The method continues by acquiring a CAT scan image of the patient's skull, as is common in patients who go to the emergency room afflicted with an intense headache.

In this step, certain images the characteristics of which may negatively affect the accuracy of the data obtained by means of the method of the invention are usually discarded. For example, images in which the image of the brain is not complete (for example, due to the image being cut off because of poor positioning of the patient), movement of the patient during imaging, images of brains containing metal parts (such as metal plates or implants), etc., are eliminated. At this point the radiologist can classify the CAT scan image obtained according to the Modified Fisher scale.

The final result of this step is a CAT scan image of the patient's skull.

3. Normalizing the Image

Normalizing the image, i.e., the skull and the brain, fundamentally consists of modifying its size and/or shape so as to adapt it to a standard skull template. This is extremely important because it allows comparing values of parameters obtained in patients of different sizes.

Indeed, while it is generally known that there has to be a certain relationship between the volume of bleeding inside the skull and the future progression of the patient, currently this knowledge is not being used objectively. Each patient has a different head size according to age, sex, and physical constitution, and therefore it is not effective to make comparisons between patients or establish thresholds above which there is a risk of death or vasospasm.

The step of normalizing the images described herein solves this problem, since it fits the patient's skull to a standard size and shape, which thereby allows making comparisons between patients, not only regarding the volume intracranial bleeding but rather regarding other parameters as well. As will be described herein in greater detail, the inventors of this application have studied the potential of predicting the future progression of the patient with respect to a plurality of parameters obtained from the normalized images of a group of patients, finding some specific parameters which allow predicting with a high probability the death of the patient and the occurrence of vasospasms.

In principle, normalization could be carried out according to any standard skull template known in the art, although the template described by the Montreal Neurological Institute (MNI) is preferably used herein. This template is described, for example, in the paper by Rorden C, Bonilha L, Fridriksson J, Bender B, and Kamath H O entitled "*Age-specific CT and MRI templates for spatial normalization*", 2012, Neuroimage 62: 91 1-922. Normalization is fundamentally performed through rotations and plastic deformations of the original image of the skull so as to adapt it to this skull template.

More specifically, the image is first trimmed to 1×1×1 mm pixel dimensions. Then a calculation is performed to provide values of the image CAT such that values of HU:-1000 . . . -100 are translated to 0 . . . 900, values of -100 . . . 100 HU are translated to 900 . . . 3100, and values of more than 100 . . . 1000 HU are translated to 3100 . . . 4000 (according to the paper by Rorden et al.). Hounsfield units (HU) constitute a quantitative scale used in computerized axial tomography studies to describe the different radiodensity levels of human tissues. Then, movement and rotation are applied to fit the center of mass and the orientation of the main axes of the skull in the image with those of the template. Finally, non-linear deformation with a number of basic functions determined from a spatial-frequency cutoff value is applied to the resulting image.

The result of this step is a normalized image of the patient's skull according to a standard template, for example, the template described in said paper by Rorden et al.

4. Obtaining the Region of Intracranial Blood

The region of intracranial blood is obtained by segmenting the image resulting from the preceding step, which only contains the patient's brain normalized according to the Rorden standard mentioned above. The spatial localization is performed by means of a brain template of the Montreal Neurological Institute.

The segmentation process can be performed in several ways, although in a preferred embodiment of the invention segmentation based on simple thresholding between 60 HU and 80 HU is carried out. That is, only pixels with a radiodensity of 60-80 HU in the normalized brain are selected. The blood outside of the brain is not included in the segmentation.

The result of this step of the present method is a region corresponding to intracranial blood including both unconnected clusters and isolated pixels. The simple thresholding used in this method diverges from extremely complex methods which often require the cooperation of a medical professional and used for purposes similar to those in prior art documents. Reference can be made to the paper by Prakash K N B, Zhou S, Morgan T C, Hanley D F, Nowinski W L. entitled "*Segmentation and quantification of intra-ventricular/cerebral hemorrhage in CT scans by modified distance regularized level set evolution technique*". International Journal of Computer Assisted Radiology and Surgery 2012; 7(5): 785-98, which describes a complex algorithm called MDRLSE (Modified Distance Regularized Level Set Evolution).

Surprisingly, despite the simplicity of the segmentation method and the existence of pixels and unconnected clusters in the result obtained, the method is proven to be sufficient for predicting the future progression of the patient according to the method of the invention. Indeed, the probability of death or vasospasm is suspected to be somehow related to the ratio between the surface and the volume of the region of subarachnoid blood. The reason is that, in general, bleeding in the subarachnoid space must be reabsorbed into the patient's brain, such that it is reasonable to think that one and the same volume of blood will be reabsorbed more rapidly, and will therefore produce less serious effects the larger the outer surface thereof is. In addition to the segmentation methods used in methods having a purpose similar to that of the present invention being much more complex, they are usually conceived for grouping the region corresponding to subarachnoid blood into connected clusters, eliminated small-sized unconnected regions and pixels. This causes the ratio between the volume and the surface of the region of intracranial blood that can be calculated from the region obtained by these methods to significantly differ from the actual ratio existing in the patient's brain. Conversely, the method based on simple thresholding used in this method allows obtaining a region of intracranial blood that more closely resembles reality, so the corresponding ratio between volume and surface of the region of intracranial blood is probably more similar to the actual ratio. This would allow the parameters which are obtained in this method to more accurately reflect the situation in the patient's brain, and therefore are more precise for predicting the patient's future progression.

The final result of this step is obtaining a region three-dimensional formed by unconnected clusters and isolated pixels corresponding to the region of intracranial blood.

5. Calculating Parameters

As described herein above, the inventors of the present application have identified a series of parameters useful for predicting the future progression of the subarachnoid hemorrhage. They are a series of geometric parameters obtained by performing various calculations based on the region of intracranial blood determined in the preceding step. These parameters are:

a) Total volume (VOL): This is the total volume of the region of intracranial blood determined in the preceding step. That is, if there are several unconnected clusters or pixels, the total volume includes the sum of the volumes of each of them.

b) Fractal dimension (FDR): The fractal dimension is a real number generalizing the concept of ordinary dimension for geometric objects that do not allow tangent space. For example, the dimension of the Koch snowflake has a topological dimension of one, but it cannot be treated as a curve; the length between any two points in the fractal (given by the Lebesgue measure) is infinite. No segment of the fractal bears any similarity to a line, but it does not bear any similarity to a part of a plane either. In a way, it could be said that it is too large to be considered a one-dimensional object, but too thin to be considered a two-dimensional object. This leads to the idea that it is possible to describe it better with a number between one and two, that is, its fractal dimension.

The fractal dimension is calculated by the known box-counting method. To that end, the fractal is pictured in a uniformly spaced grid and the number of boxes needed to cover the set are counted. The box-counting dimension is calculated by seeing how this number changes as the grid becomes thinner by applying this algorithm. By way of example, reference can be made to the paper by Nirupam Sarkar et al. "*An efficient differential box-counting approach to compute fractal dimension of an image*", IEEE Transactions on systems, man and cybernetics, Volume 24, Issue 1, January 1994.

c) Surface-volume (SRAVOL) ratio: This is the ratio between the previously defined volume (VOL) and the total area of the outer surface of the region of intracranial blood determined in the preceding step. That is, the total surface will include the sum of the outer surfaces of each of the various unconnected clusters or pixels constituting the region determined in the preceding step. As mentioned, the surface-volume ratio is important in this context because the capacity of brain tissue to reabsorb intracranial blood may be dependent on the surface of the region corresponding to intracranial blood. Namely, a high surface-volume ratio may be indicative of a higher reabsorption capacity and therefore of a lower severity of the patient's condition.

The final result of this step is the obtaining of a plurality of parameters which reflect in some way the characteristics of the region of intracranial subarachnoid blood obtained in the preceding step.

6. Determining the Risks of Death and Vasospasm

Once the preceding parameters are obtained, they are analyzed to determine the probability of the death of the patient occurring or of the patient suffering vasospasms.

To determine the expressions which allow predicting the future progression of the patient the inventors of the present application were provided with all the data of a group of patients who went to a hospital due to a subarachnoid hemorrhage. This data includes both personal data (age, sex, etc.) and the data obtained upon arrival to the hospital (cerebral CAT scan, the different classifications according to Fisher, Hunt, and WFNS, etc.) and data relating to the final result of the patient's visit to the hospital (occurrence of vasospasm, death, release, etc.).

The CAT scan images of these patients were processed as described herein to obtain the respective regions of intracranial blood from the normalized brain image. Then, multiple parameters were calculated from the respective regions of normalized intracranial blood. These parameters included but were not limited to the parameters described in the preceding step. Then a statistical analysis of all the parameters (including both the parameters calculated from the brain images and additional parameters such as the Fisher, Hunt, and WFNS classifications, and personal data such as sex and age) was performed to determine which of them are relevant for predicting death or the occurrence of vasospasm. As a result, the expressions described below were obtained, and in said expressions only the parameters shown to be relevant are present.

6a. Death

Preferably this probability is determined according to at least the following parameters: surface-volume (SRAVOL) ratio, patient classification grade on a WFNS (WFNS) scale, and the age (AGE) and sex (SEX) of the patient.

More preferably, this probability is calculated by means of the following formula:

$$p_{death} = \frac{e^A}{1+e^A}$$

where $A=C+A_1*SRAVOL+A_2*AGE+A_3*SEX+A_4*WFNS$
C, A1, A2, A3, A4 are constants,
SRAVOL is the surface-volume ratio of the region calculated,
SEX is coded as 0->man, 1->woman,
WFNS is the patient classification grade on the WFNS scale of Table 2.

Coefficients C, A1, A2, A3, A4 are obtained from a bivariate logistic regression based on actual patient data.

6b. Vasospasm

Preferably this probability is determined according to at least the following parameters: volume (VOL), fractal dimension (FDR), and patient classification grade on a Hunt and Hess (HUNT_HESS) scale.

More preferably, this probability p is calculated by means of following formula:

$$p_{vasospasm} = \frac{e^{A'}}{1+e^{A'}}$$

where $A'=C'+A'_1*VOL+A'_2*FDR+A'_3*Hunt\_Hess$
C', A'1, A'2, A'3 are constants,
VOL is volume of the region calculated,
FDR is the fractal dimension,
Hunt and Hess is the patient classification grade on the Hunt and Hess scale of Table 1.

Coefficients C, A'1, A'2, A'3 are obtained from a bivariate logistic regression based on actual patient data.

The present invention therefore allows establishing a specific cutoff value for the probability of death ($p_{death}$) or vasospasm ($p_{vasospasm}$) that allows an initial classification of patients upon their arrival to an emergency room according to their severity. This would allow prioritizing treatment for those patients who are the most severe, leaving in a waiting room those patients showing a lower severity.

For example, $p_{vasospasm}$ cut-off value=0.5 (or $p_{death}$ cut-off value=0.5) could be used to separate patients into those having a higher probability of suffering vasospasm (or death) and those having lower probability of suffering vasospasm (or death). That is, patients with a probability of vasospasm $p_{vasospasm}$>0.5 (greater than 50%) would receive care first and patients with a probability of vasospasm $p_{vasospasm}$<0.5 (less than 50%) could be made to wait. Similarly, patients with a probability of death $p_{death}$>0.5 (greater than 50%) would receive care first and patients with a probability of death $p_{death}$<0.5 (less than 50%) could be made to wait.

It must be noted that the use of a cut-off value of 0.5 cut-off value is only a particular example, but it would be possible to use other different cut-off values according to the amount of allowable false negatives. For example, the cut-off value both for death and for vasospasm could be set at $p_{vasospasm}$=0.4 (or $p_{death}$=0.4), or even at $p_{vasospasm}$=0.3 (or $p_{death}$=0.3), if the probability of false negatives (i.e., the probability of making a patient wait due to a low probability of vasospasm or death who in the end suffers one of the two) is to be prevented as much as possible. That is, patients with a probability of vasospasm $p_{vasospasm}$>0.4 (greater than 40%) would receive care first and could be made to wait patients with a probability of vasospasm $p_{vasospasm}$<0.4 (less than 40%). Similarly, patients with a probability of death $p_{death}$>0.4 (greater than 40%) would receive care first and patients with a probability of death $p_{death}$<0.4 (less than 40%) could be made to wait.

Moreover, it must be noted that if the Hunt and Hess classification grade, the WFNS classification grade, and the age and sex of the patient are known, and a tomography of the patient's skull is available, it would be possible to perform this method without having direct contact with the patient. The method of the invention could be carried out remotely based on that data and the corresponding parameters could be calculated from said data to predict death or vasospasm.

This method can be carried out in a completely or partially automated manner by processing means. Although the processing means can be integrated in the actual computerized tomography (CAT) scan imaging apparatus, it is understood that this is not limiting in the present invention. In general, the method could be carried out with any other processing means to which the images CAT of the patient's skull are provided. Therefore, the invention also extends to computer programs adapted so that any of such processing means can carry out to practice said processes. Such programs can be in the form of source code, object code, an intermediate source code and object code, for example, in partially compiled form, or in any other form suitable for use in carrying out to practice the processes according to the invention. The computer programs also cover cloud applications based on said method.

In particular, the invention covers computer programs arranged on or in a carrier. The carrier can be any entity or device capable of supporting the computer program. When the program is incorporated in a signal that can be transported directly by a cable or other device or means, the carrier can be made up of said cable or other device or means. As a variant, the carrier could be an integrated circuit in which the computer program is included, the integrated circuit being adapted for executing, or for being used in the execution of, the corresponding processes.

For example, the programs could be incorporated in a storage medium, such as a ROM memory, a CD ROM memory or a semiconductor ROM memory, a USB memory, or a magnetic recording medium, for example, a floppy disk or a hard drive. Alternatively, the programs could be supported in a transmittable carrier signal. For example, it could be an electrical or optical signal that could be transported through an electrical or optical cable, by radio, or by any other means.

In summary, the method of the present invention provides a tool for medical professionals for predicting the probability of death and vasospasm in patients afflicted with subarachnoid hemorrhage. This information can be used to perform an initial classification of patients upon their entry in a hospital, dedicating more time and resources to those patients whose probable future progression includes the occurrence of vasospasms or death. The use of the available resources would thereby be optimized, and care for those patients with higher risks would be improved.

PREFERRED EMBODIMENT OF THE INVENTION

Obtaining the Prediction Models

Figure 1:
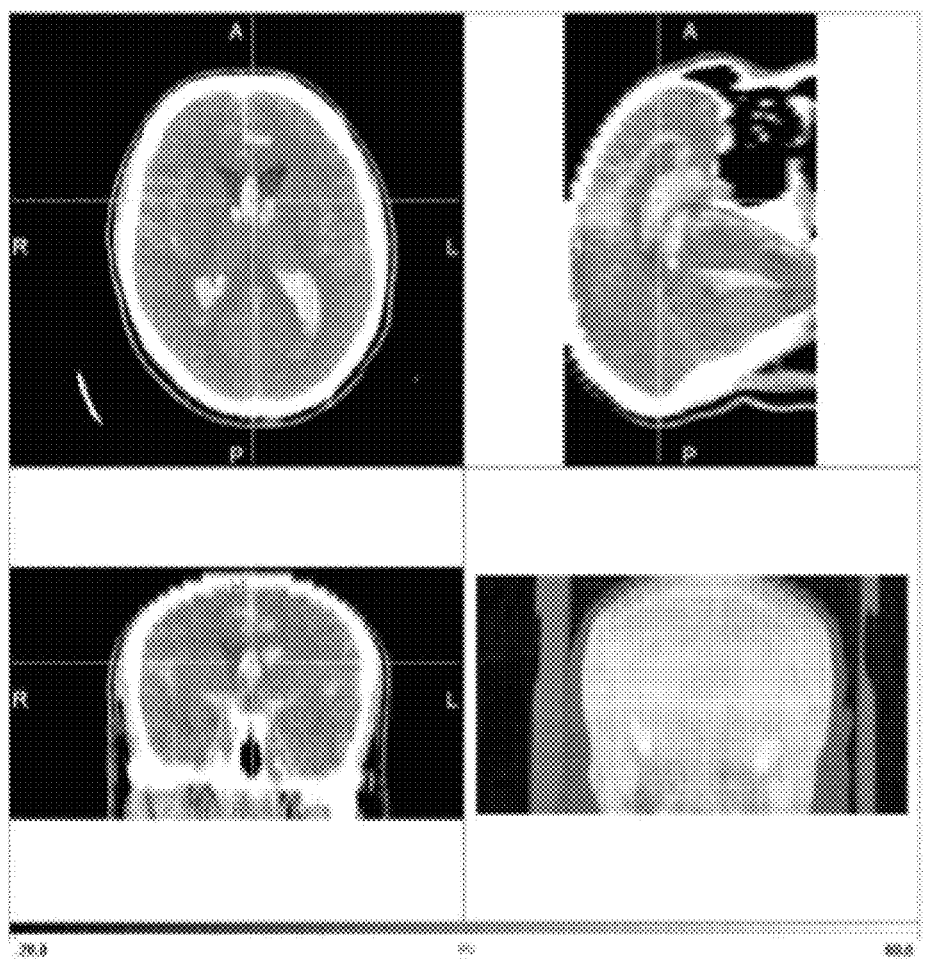
FIG. 1 shows original CAT scan images corresponding to the skull of a first patient

The data of 85 patients with a detected subarachnoid hemorrhage obtained from different hospitals was used. Binary logistic regression was selected to develop the prediction model. A large number of variables of image, clinical, and demographic variables were initially selected in the conditional backward test (eleven variables: WFNS classification grade, Hunt and Hess classification grade, and Fisher classification grade, age, sex, surface-volume ratio, sphericity, fractal dimension, volume, surface, diameter). All these variables have been defined hereinabove with the exception of the sphericity and the diameter, which are described below.

Sphericity (SPH): is a parameter unitless adopting a value between 0 and 1 which indicates the extent to which the region corresponding to intracranial blood obtained resembles a sphere. It is calculated according to the expression:

$$\pi^{1/3}(6V)^{2/3}/A$$

where V is the object volume,
A is its surface.

Diameter is the maximum distance between the pixels of the region corresponding to intracranial blood obtained.

The modelling was done in scales. The variable which, when eliminated, causes the least change in model likelihood logarithm, which furthermore had a significance of more than 0.1, has been excluded in each scale.

In the model relating to death of the patient, the same group of parameters was arrived in backward and forward modelling. Namely, the parameters were: surface-volume ratio, age, sex, and WFNS classification grade. A constant C has been included in the death prediction model.

The specific expression was:

$$p_{death} = \frac{e^A}{1 + e^A}$$

where $A = C + A_1 * SRAVOL + A_2 * AGE + A_3 * SEX + A_4 * WFNS$
C, A1, A2, A3, A4 are constants,
SRAVOL is the surface-volume ratio of the region calculated,
SEX is coded as 0->man, 1->woman,
WFNS is the patient classification grade on the WFNS scale.

Using this expression, death of the patient was prognosticated if the probability calculated by preceding expression was greater than 0.5. Using this criterion, the prediction of survival for the aforementioned group of 85 patients was correct in 91% of the patients and the prediction of death was correct in 71% of the patients (see Table 4).

TABLE 4

Prediction of death statistics

|  | Prediction | | |
|---|---|---|---|
|  | Death | | Percentage |
|  | NO | YES | correct |
| Actual observed Death NO | 56 | 5 | 91.8 |
| YES | 7 | 17 | 70.8 |
| Total percentage |  |  | 85.9 |

Moreover, in the vasospasm occurrence model, the best result has been obtained in the conditional backward test. The parameters which finally formed the model were: volume, fractal dimension, and Hunt and Hess. This model also includes a constant C.

$$p_{vasospasm} = \frac{e^{A'}}{1 + e^{A'}}$$

where $A' = C^* + A'_1 * VOL + A'_2 * FDR + A'_3 * Hunt\_Hess$
C', A'1, A'2, A'3, A'4 are constants.
VOL is volume of the region calculated,
FDR is the fractal dimension,
Hunt and Hess is the patient classification grade on the scale Hunt and Hess of Table 1.

Using this expression and using 0.5 as a cut-off value, the vasospasm occurrence prediction was correct in 54% of the patients and the vasospasm non-occurrence prediction was correct in 64% of the patients (see Table 5).

TABLE 5

Vasospasm prediction statistics

|  | Prediction | | |
|---|---|---|---|
|  | Vasospasm | | Percentage |
|  | NO | YES | correct |
| Actual observed Death NO | 30 | 17 | 63.8 |
| YES | 16 | 19 | 54.3 |
| Total percentage |  |  | 59.8 |

Moreover, studies relating to individual parameters as predictors of the future progression of the patient in relation to death and the occurrence of vasospasm were also performed. Table 6 shows the cut-off values obtained with individual parameters (SRAVOL, VOL, SPH, FDR, WFNS, and Hunt and Hess) and with the model (value of A and A' in sections 6a and 6b) in relation to the prediction of in-hospital death or vasospasm.

TABLE 6

Sensitivity and threshold for individual parameters and model of the in-hospital death and vasospasm panel. Only statistically significant biomarkers are listed.

| Variable | sensitivity @90% specificity | Cut-off value for 90% specificity | sensitivity @80% specificity | Cut-off value for 80% specificity |
|---|---|---|---|---|
| In-hospital death | | | | |
| SRAVOL (cm$^{-1}$)* | 58% | 25.9 | 75% | 31.5 |
| VOL (mL) | 46% | 34.0 | 75% | 22.5 |
| SPH | 38% | 6.93 | 67% | 5.62 |
| FDR | 42% | 2.05 | 58% | 1.97 |
| WFNS | 31%[a] | 4 | 54%[b] | 3 |
| Hunt and Hess | 25%[c] | 4 | 49%[d] | 3 |
| Model | 75% | 0.416 | 83% | 0.293 |
| Vasospasm | | | | |
| WFNS | 13% |  | 26% | 4 |
| Hunt and Hess | 13% |  | 29% | 4 |
| forward model | 20% | 0.629 | 34% | 0.561 |
| backward model | 13% |  | 29% |  |

*the lower the value of the SRAVOL, the more probable death is.
[a]for WFNS > 4, sensitivity is 45.8%.
[b]for WFNS > 3, sensitivity is 50.8%.
[c]for Hunt and Hess > 4, sensitivity is 45.8%.
[d]for Hunt and Hess > 3, sensitivity is 54.1%.
These discrepancies are due to the categorical nature of both variables, which is a type of assumed scale here.

The values of this table are interpreted as follows. For example, in relation to the prediction of in-hospital death, if 100 patients have a surface-volume ratio less than 25.9 cm$^{-1}$ (SRAVOL<25.9 cm$^1$), 58 of them will die (sensitivity*100). Similarly, if 100 patients have a surface-volume ratio less than 25.9 cm$^{-1}$ (SRAVOL>25.9 cm$^1$), and 90 will survive (100*specificity). In another example, if 100 patients have a fractal dimension greater than 1.97 (FDR>1.97), 58 of them will die (sensitivity*100). Similarly, if 100 patients have a fractal dimension less than 1.97 (FDR<1.97), 80 will survive (specificity*100) are going to survive. This interpretation is valid for each variable in Table 6 with the exception of that corresponding to the model, since the value thereof represents a linear combination lineal of individual parameters.

As can be seen, by using individual parameters statistically significant results are obtained, although the results are lower than those obtained by the models that were finally selected. The power of the two models developed can be seen in cases in which, based only on individual requirements, a result that actually cannot be produced is predicted. For example, in the group of 85 patients with a subarachnoid hemorrhage on which the study was performed there were 6 patients who met the six individual requirements with an 80% specificity of death according to Table 6, but who ultimately did not die. Of these 6 patients, the death prediction model correctly predicted the survival of three of them. Similarly, in the group of patients there were 11 patients who did not meet the individual requirements for vasospasm with a specificity of 80% (WFNS≤4, Hunt and Hess≤4), but who ultimately suffered a vasospasm. The vasospasm prediction model correctly predicted the occurrence of a vasospasm in the 11 patients.

In summary, although the success rates of Tables 4 and 5 using the probability of 0.5 as the cut-off value may not seem very high, particularly those of Table 5, they represent an enormous improvement over the complete absence of objective information at present. It must be taken into account that these patients normally arrive at the emergency room of a hospital where many times medical professionals are overwhelmed with patients, such that the time and resources dedicated to caring for each one of them are fundamental variables that may negatively affect the quality of the medical care provided. Furthermore, it must be noted that as mentioned hereinabove, it would be possible to use different cut-off values to even further minimize the possibility of false negatives.

The method of the present invention allows initially prioritizing the patients afflicted with subarachnoid hemorrhage, for example, such that those for whom death or a vasospasm is not predicted receive care after other patients for whom receiving care is more urgent, either because of a subarachnoid hemorrhage or another cause. It must be noted that by using the cut-off value of 0.5, the success rate of the death model when it predicts survival of the patient ($p_{death}$<0.5) is 91.8%, and the success rate of the vasospasm model when it predicts vasospasm non-occurrence ($p_{vasospasm}$<0.5) is 63.8%. Therefore, in specific cases the medical professional can make the decision to make these patients wait in order to care for other patients in which the severity is greater with reasonable guarantees.

Examples of Patients

The data obtained for some of the patients, the prediction obtained using the described models, and the final outcome of progression are described below.

Patient 1

Figure 2:
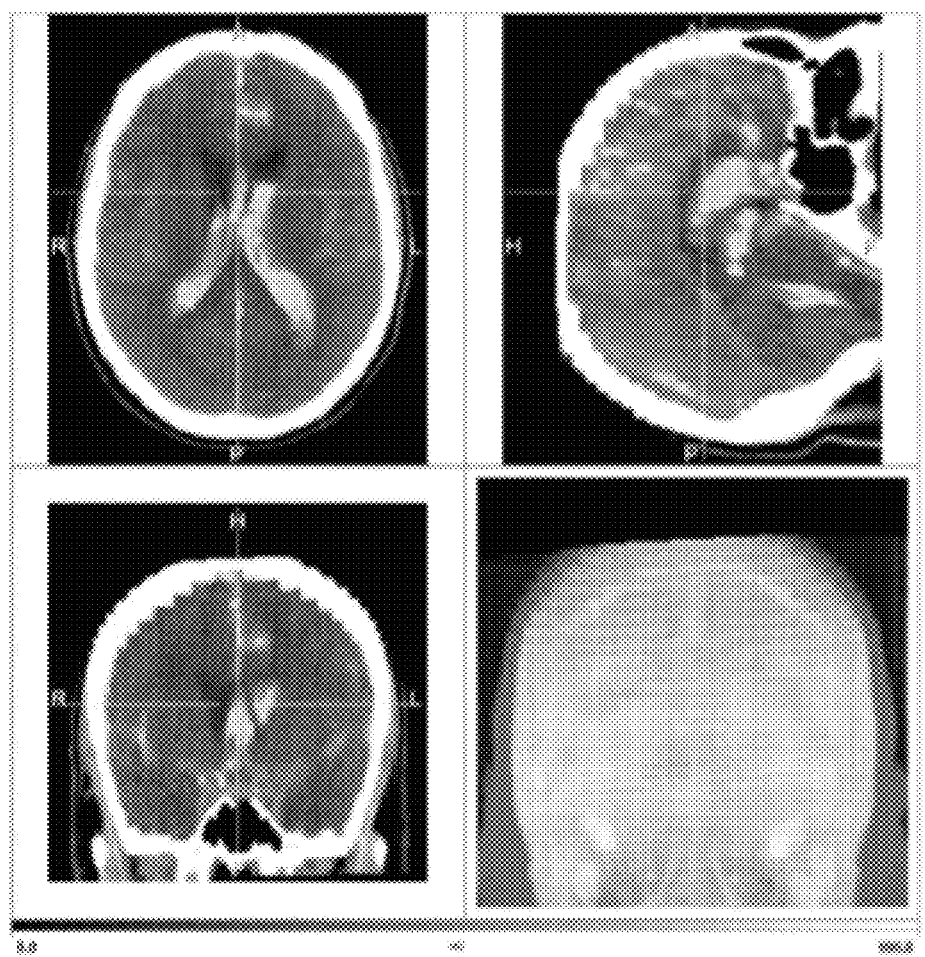
FIG. 2 shows normalized CAT scan images of the skull of the first patient in which the areas corresponding to intracranial blood have been highlighted.

FIG. 1 shows the CAT scan image of the skull initially obtained for a first patient, male, 39 years of age, with a subarachnoid hemorrhage. According to this method, the initial CAT scan image was normalized, and segmentation between 60-80 HU was performed to detect the region corresponding to intracranial blood. FIG. 2 shows the CAT scan image of the patient's skull now normalized and with the region of intracranial blood highlighted in light grey. As can be seen, the region of intracranial bleeding is very fragmented and is primarily located in the space between the two cerebral hemispheres. This patient suffered a vasospasm and died in the hospital.

The region of intracranial blood obtained from the normalized CAT scan image had a volume 23 mL, a surface of 777 cm$^2$, a low sphericity of 5.03%, a diameter close to that of the brain (17.58 cm), a surface-volume ratio of 33.75 cm$^{-1}$, and a fractal dimension of 1.9. The death prediction model yielded a result $p_{death}$=0.550>0.5, therefore it correctly predicted the death of the patient (true positive). The vasospasm prediction model yielded a result $p_{vasospasm}$=0 614>0.5, therefore it correctly predicted vasospasm occurrence (true positive). The Patient's Hunt and Hess grade was 5 and WFNS grade was 5. The patient furthermore complied with an individual predictor derived from the image of in-hospital death characteristics (volume>22.5 mL for 80% specificity), in addition to the Hunt and Hess and WFNS predictors.

Figure 3:
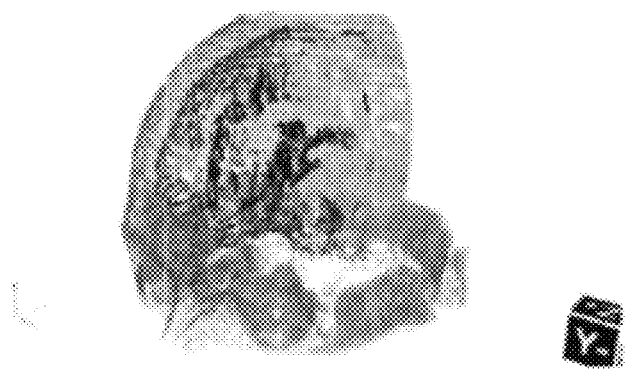
FIG. 3 shows three-dimensional images of the normalized brain and the region of intracranial blood of the first patient.
Figure 4A:
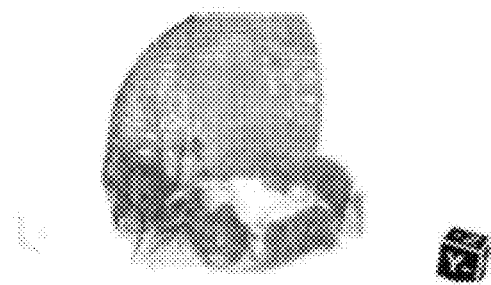
FIGS. 4a and 4b respectively show a three-dimensional image of the normalized brain and of the region of intracranial blood of the first patient.
Figure 4B:

FIG. 3 shows the patient's brain with the region corresponding to intracranial blood being highlighted. FIGS. 4a and 4b show the brain (FIG. 4a) and the region of intracranial blood (FIG. 4b), respectively, in an isolated manner.

Patient 2

Figure 5:
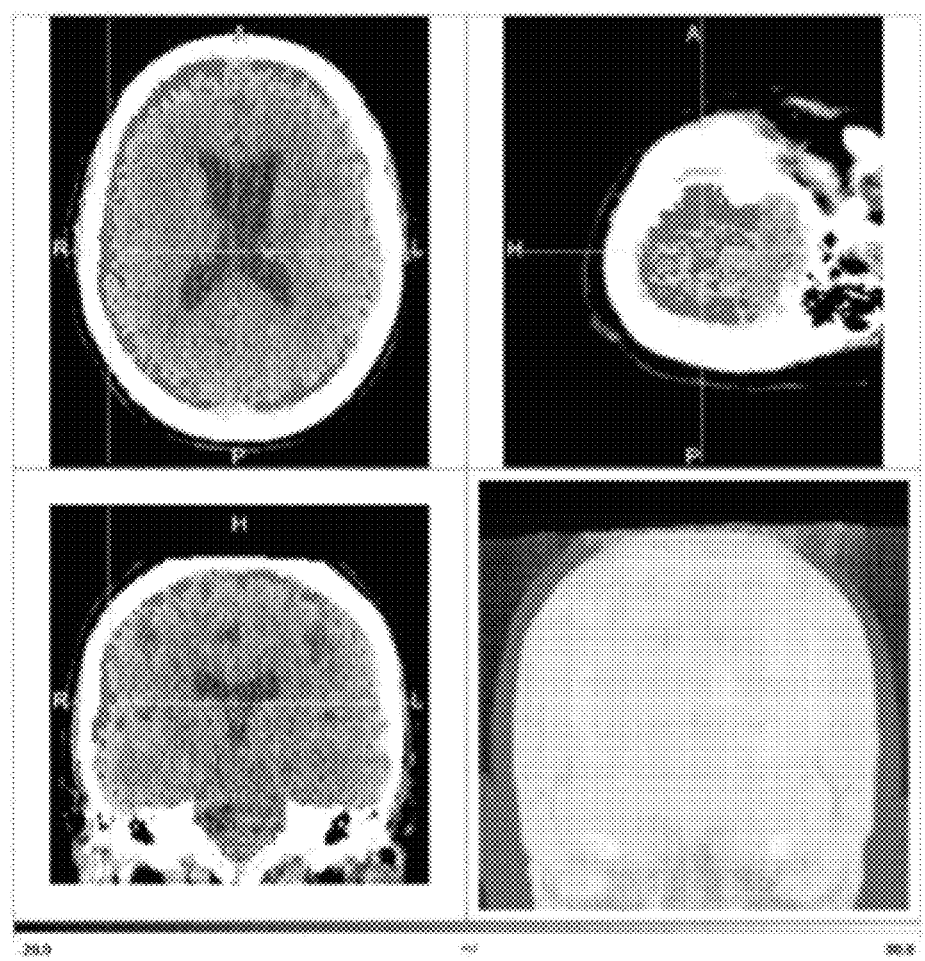
FIG. 5 shows normalized CAT scan images of the skull of a second patient in which the areas corresponding to intracranial blood have been highlighted.

This second patient was a man, 54 years of age, with a subarachnoid hemorrhage who died in the hospital without suffering a vasospasm. FIG. 5 shows a normalized CAT scan image of the patient's skull with the region corresponding to intracranial blood being highlighted in light grey. The region of intracranial blood obtained from this image had a volume of 95 mL, a surface of 1654 cm$^2$, a sphericity of 6.1%, a diameter close to that of the brain (17.7 cm), a surface-volume ratio of 17.4 cm$^{-1}$, and a fractal dimension of 2.1. The death prediction model yielded a result $p_{death}$=0.762>0.5, therefore it correctly predicted the death of the patient (true positive). The vasospasm occurrence prediction model yielded a result $p_{vasospasm}$=0.04<0.5, therefore it correctly predicted vasospasm non-occurrence (true negative). The patient had a Hunt and Hess score of 1 and WFNS score of 2. The patient met individual predictors derived from the image of in-hospital death characteristics (volume>22.5 mL, surface-volume ratio<31.5 cm$^{-1}$, sphericity>5.62%, fractal dimension>1.97 with 80% of specificity).

Patient 3

Figure 6:
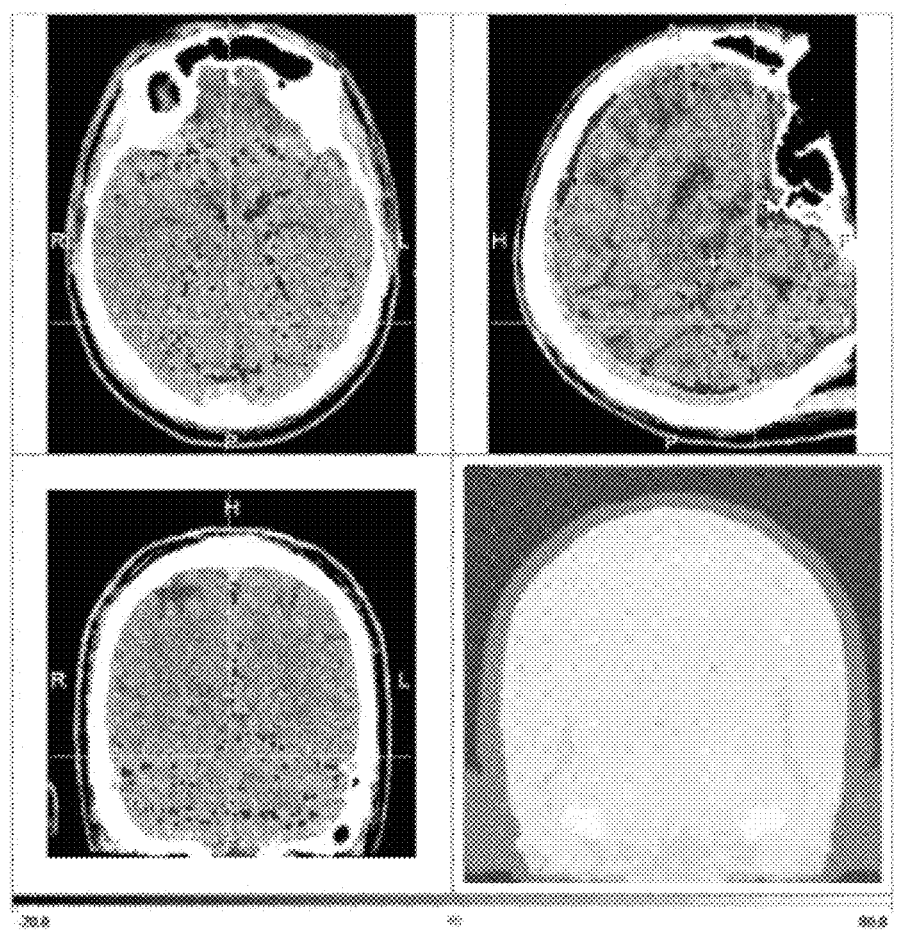
FIG. 6 shows normalized CAT scan images of the skull of a third patient in which the areas corresponding to intracranial blood have been highlighted.

This third patient was a man, 69 years of age, with a subarachnoid hemorrhage who did not die and did not suffer a vasospasm. FIG. 6 shows a normalized CAT scan image of the patient's skull with the region corresponding to intracranial blood being highlighted in light grey. The region of intracranial blood obtained from this normalized CAT scan image had a volume of 18 mL, a surface of 851 cm$^2$, a low sphericity of 3.9%, a diameter close to that of the brain (17.4 cm), a surface-volume ratio of 46.4 cm$^{-1}$ and a fractal dimension of 1.6. The death prediction model yielded a result $p_{death}$=0.234<0.5, therefore it correctly predicted the survival of the patient (true negative). The vasospasm prediction model yielded a result $p_{vasospasm}$=0.197<0.5, therefore it correctly predicted vasospasm non-occurrence (true negative). The patient had a Hunt and Hess score of 2 and WFNS score of 2. The patient did not meet any individual predictor derived from the image of death characteristics with 80% specificity

The invention claimed is:

1. A method for predicting or prognosticating the probability of death or vasospasm in a patient with a subarachnoid hemorrhage, characterized in that it comprises the following steps:
   performing a clinical assessment of the patient according to the Hunt and Hess (RUNT HESS) scale and the World Federation of Neurosurgeons (WFNS) scale and determining patient sex (SEX) and age (AGE);
   obtaining a computerized axial tomography scan image of the patient's skull;
   normalizing the computerized axial tomography scan image obtained from the patient's skull according to a standard skull template to form a normalized image;
   obtaining a region corresponding to intracranial blood by segmenting the normalized image of the patient's skull, wherein the region corresponding to intracranial blood comprises performing segmentation based on simple thresholding between 60 HU and 80 HU;
   calculating at least the following parameters of the region of intracranial blood obtained: total volume (VOL), fractal dimension (FDR), and surface-volume (SRA-VOL) ratio; and
   determining the probability of death or vasospasm in the patient according to at least the parameters calculated.

2. The method according to claim 1, wherein the probability of death of the patient is determined according to at least the following parameters: surface-volume (SRAVOL) ratio, patient classification grade on a WFNS (WFNS) scale, the age (AGE) and sex (SEX) of the patient.

3. The method according to claim 2., wherein the probability of death of the patient is determined according to the following expression:

$$p_{death} = \frac{e^A}{1+e^A}$$

where $A = C + A_1*SRAVOL + A_2*AGE + A_3*SEX + A_4*WFNS$

C, A1, A2, A3, A4 are constants,
SRAVOL is the surface-volume ratio of the region calculated,
SEX is coded as 0->man, 1->woman,
WFNS is the patient classification grade on the WFNS scale .

4. The method according to claim I, wherein the probability of the patient suffering a vasospasm is determined according to at least the following parameters: volume (VOL), fractal dimension (FDR), and patient classification grade on a Hunt and Hess (HUNT_HESS) scale.

5. The method according to claim 4, wherein the probability of the patient suffering a vasospasm is determined according to the following expression:

$$p_{vasospasm} = \frac{e^{A'}}{1+e^{A'}}$$

PS where $A' = C' + A'_1*VOL + A'_2*FDR + A'_3*HUNT\_HESS$
C', A'1, A'2, A'3 are constants,
VOL is volume of the region calculated,
FDR is the fractal dimension,
HUNT_HESS is the patient classification grade on the Hunt and Hess scale.

6. The method according to claim 1, wherein the step of normalizing the computerized axial tomograph scan image of the patient's skull comprises performing rotations and plastic deformations of said image so as to adapt it to the standard skull template.

7. A non-transitory computer readable medium storing a computer program comprising computer program instruction for causing a computer carry to out the method of claim 1, the non-transitory computer readable medium not constituting a transitory signal.

* * * * *